(12) United States Patent
Fukuda

(10) Patent No.: US 10,796,420 B2
(45) Date of Patent: Oct. 6, 2020

(54) ENERGY SUBTRACTION PROCESSING APPARATUS, METHOD, AND PROGRAM

(71) Applicant: FUJIFILM Corporation, Tokyo (JP)

(72) Inventor: Wataru Fukuda, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 255 days.

(21) Appl. No.: 15/885,816

(22) Filed: Feb. 1, 2018

(65) Prior Publication Data

US 2018/0240224 A1 Aug. 23, 2018

(30) Foreign Application Priority Data

Feb. 21, 2017 (JP) .................................. 2017-030307

(51) Int. Cl.
| | | |
|---|---|---|
| *G06T 5/50* | (2006.01) | |
| *G06T 7/00* | (2017.01) | |
| *G01B 15/02* | (2006.01) | |
| *A61B 5/00* | (2006.01) | |

(52) U.S. Cl.
CPC .............. *G06T 5/50* (2013.01); *G01B 15/025* (2013.01); *G06T 7/0014* (2013.01); *A61B 5/4312* (2013.01); *G06T 2207/10016* (2013.01); *G06T 2207/10116* (2013.01); *G06T 2207/20221* (2013.01); *G06T 2207/20224* (2013.01); *G06T 2207/30068* (2013.01)

(58) Field of Classification Search
None
See application file for complete search history.

(56) References Cited

U.S. PATENT DOCUMENTS

| | | | | |
|---|---|---|---|---|
| 8,340,380 B2 | 12/2012 | Morita | | |
| 8,600,126 B2* | 12/2013 | Morita | ..................... | G06T 5/008 |
| | | | | 382/128 |
| 8,738,124 B2* | 5/2014 | Davies | ................... | A61B 6/482 |
| | | | | 600/547 |
| 9,168,013 B2* | 10/2015 | Roessl | ................... | A61B 6/488 |
| 2009/0010380 A1* | 1/2009 | Gotoh | ................... | A61B 6/481 |
| | | | | 378/5 |

(Continued)

FOREIGN PATENT DOCUMENTS

JP 2010253245 11/2010

*Primary Examiner* — Nancy Bitar
(74) *Attorney, Agent, or Firm* — JCIPRNET

(57) ABSTRACT

In an energy subtraction processing apparatus, method, and a non-transitory computer readable recording medium storing program, a high-quality image is generated by acquiring an absorption coefficient suitable for a subject. A subject information acquisition unit acquires the thickness information of a breast and a mammary gland content rate, as subject information, based on a low voltage image acquired by energy subtraction imaging. An absorption coefficient acquisition unit acquires an absorption coefficient corresponding to the subject information with reference to the relationship between the thickness of the breast and the X-ray absorption coefficient, which is calculated in advance. Based on the absorption coefficient acquired by the absorption coefficient acquisition unit, a weighting coefficient calculation unit calculates a weighting coefficient at the time of performing energy subtraction processing. A subtraction unit performs subtraction processing using the weighting coefficient calculated by the weighting coefficient calculation unit.

12 Claims, 8 Drawing Sheets

(56) References Cited

U.S. PATENT DOCUMENTS

| | | | | |
|---|---|---|---|---|
| 2009/0118614 A1* | 5/2009 | Sendai | ............... | A61B 6/037 |
| | | | | 600/437 |
| 2009/0304253 A1* | 12/2009 | Puong | ............... | G06T 5/50 |
| | | | | 382/131 |
| 2009/0323896 A1* | 12/2009 | Kitamura | ............... | A61B 6/00 |
| | | | | 378/98.11 |
| 2010/0321404 A1* | 12/2010 | Fischer | ............... | A61B 6/583 |
| | | | | 345/632 |
| 2015/0093013 A1* | 4/2015 | Morita | ............... | A61B 6/5205 |
| | | | | 382/132 |
| 2015/0327829 A1* | 11/2015 | Morita | ............... | A61B 6/502 |
| | | | | 378/37 |
| 2016/0213344 A1* | 7/2016 | Yi | ............... | A61B 6/5282 |
| 2016/0350910 A1* | 12/2016 | Jeong | ............... | G06K 9/52 |
| 2017/0116730 A1* | 4/2017 | Yamanaka | ............... | G06T 5/008 |
| 2017/0231593 A1* | 8/2017 | Fukuda | ............... | A61B 6/5241 |
| | | | | 382/132 |
| 2018/0279982 A1* | 10/2018 | Fukuda | ............... | A61B 6/502 |

\* cited by examiner

ENERGY SUBTRACTION PROCESSING APPARATUS, METHOD, AND PROGRAM

CROSS-REFERENCE TO RELATED APPLICATIONS

The present application claims priority under 35 U.S.C. § 119 to Japanese Patent Application No. 2017-030307, filed on Feb. 21, 2017. Each of the above application(s) is hereby expressly incorporated by reference, in its entirety, into the present application.

BACKGROUND OF THE INVENTION

1. Field of the Invention

The present invention relates to an energy subtraction processing apparatus, method, and a non-transitory computer readable recording medium storing program for generating a subtraction image, in which a specific structure of a subject included in a radiographic image has been extracted, by performing weighting subtraction between two radiographic images.

2. Description of the Related Art

Energy subtraction processing using two radiographic images, which are obtained by irradiating a subject with two types of radiation having different energy distributions, based on the fact that the attenuation amount of transmitted radiation differs depending on the substance forming the subject has been known. The energy subtraction processing is a method of acquiring an image in which a specific structure has been extracted by making respective pixels of the two radiographic images obtained as described above correspond to each other, multiplying the pixels by an appropriate weighting coefficient, and then performing subtraction therebetween. By performing such energy subtraction processing, for example, by generating a soft part image in which a bone part has been removed from a radiographic image obtained by imaging a chest part, it is possible to observe a shadow that appears in the soft part without being obstructed by the bone. Conversely, by generating a bone part image in which a soft part has been removed, it is possible to observe a shadow appearing in the bone part without being disturbed by the soft part.

Energy subtraction processing on radiographic images of a breast in a radiographic image capturing apparatus (called a mammography) for imaging the breast is also known. The breast is mainly formed of mammary gland tissues and adipose tissues, and it is important for diagnosis to find a lesion hidden in the mammary gland tissue. Therefore, by generating a subtraction image in which the mammary gland tissue in the breast has been extracted, it is possible to find a lesion hidden in the mammary gland tissue.

Energy subtraction processing in mammography is performed as follows. That is, using the fact that mammary glands and fat forming the breast have different radiation absorbances for radiations having different energies, radiations having different energies are emitted to the breast to obtain two radiographic images. Then, an energy subtraction image in which adipose tissue has been removed and mammary gland tissue has been extracted is acquired by multiplying the two radiographic images by a weighting coefficient and then performing subtraction therebetween.

Here, the proportion of mammary glands in the breast is called a mammary gland content rate. The mammary gland content rate is very useful for accurately ascertaining the characteristics of the breast, and this is medically indispensable information. For example, research suggests that there is a correlation between the mammary gland content rate and the risk of carcinogenesis. For this reason, various methods for calculating the mammary gland content rate have been proposed. For example, JP2010-253245A has proposed a method in which a fat image, which is an image having a pixel value in a case where all the mammary gland tissues of the breast are replaced with adipose tissues, is generated from a breast image acquired by mammography and the mammary gland content rate is calculated based on the relationship between the breast image and the fat image.

Incidentally, in the case of generating a subtraction image in which mammary gland tissue has been extracted, weighting subtraction between an image acquired by low voltage imaging (hereinafter, referred to as a low voltage image) and an image acquired by high voltage imaging (hereinafter, referred to as a high voltage image) is performed using a weighting coefficient determined by the ratio of a difference between an absorption coefficient of radiation in the mammary glands and fat in the case of performing imaging with low energy radiation (hereinafter, referred to as low voltage imaging) and an absorption coefficient of radiation in the mammary glands and fat in the case of performing imaging with high energy radiation (hereinafter, referred to as high voltage imaging).

SUMMARY OF THE INVENTION

The substance has an absorption coefficient of radiation depending on the energy of the radiation. In addition, in a case where the radiation emitted to the subject is not monochromatic but distributed in a certain energy range, a phenomenon called beam hardening occurs in which the energy distribution of the detected radiation (for example, radiation emitted to the detector) changes depending on the thickness of the substance (mammary glands and fat in the breast) contained in the subject. For this reason, the absorption coefficient changes depending on the thickness and composition of the subject. Here, in a case where the absorption coefficient is not appropriately calculated, the structure contained in the subject cannot be accurately extracted even if the energy subtraction processing is performed, so that the subtraction image includes artifacts. Therefore, in order to accurately extract a target structure in the subtraction image, it is necessary to determine the absorption coefficient in consideration of the thickness or composition of the substance forming the subject.

Here, it is possible to calculate the mammary gland content rate by using the method disclosed in JP2010-253245A. However, in the method disclosed in JP2010-253245A, the absorption coefficient of a substance, which is necessary for performing subtraction processing, is not acquired.

The invention has been made in view of the above circumstances, and it is an object of the invention to generate a high-quality subtraction image by acquiring an absorption coefficient suitable for a subject in the case of performing energy subtraction processing.

An energy subtraction processing apparatus according to the invention comprises: an image acquisition unit that acquires two radiographic images with radiations transmitted through a subject and having different energy distributions; a subject information acquisition unit that acquires subject information including thickness information of the subject based on at least one of the two radiographic images;

an absorption coefficient acquisition unit that acquires an absorption coefficient corresponding to the subject information with reference to a relationship between a thickness of the subject and an absorption coefficient of the radiation, which is calculated in advance according to the energy distribution and a substance forming the subject; an weighting coefficient calculation unit that calculates, based on the acquired absorption coefficient, a weighting coefficient in a case of performing weighting subtraction between corresponding pixels of the two radiographic images; and a subtraction unit that generates a subtraction image, in which a specific structure of the subject has been extracted, by performing weighting subtraction between the corresponding pixels of the two radiographic images using the weighting coefficient.

In the energy subtraction processing apparatus according to the invention, the subject information acquisition unit may acquire the subject information by analyzing at least one of the two radiographic images.

In the energy subtraction processing apparatus according to the invention, the subject information acquisition unit may acquire the subject information based on a radiographic image acquired with radiation having a low energy distribution between the two radiographic images.

In the energy subtraction processing apparatus according to the invention, the subject information acquisition unit may further acquire composition information of the subject as the subject information.

In the energy subtraction processing apparatus according to the invention, the subject may be a breast, the thickness information may be a thickness of the breast, and the composition information may be a mammary gland content rate.

In the energy subtraction processing apparatus according to the invention, the subject information acquisition unit may calculate the thickness information and the composition information based on the two radiographic images, a tube voltage at the time of imaging, and the relationship between the thickness of the subject and the absorption coefficient of the radiation.

In the energy subtraction processing apparatus according to the invention, the subject information acquisition unit and the absorption coefficient acquisition unit may acquire an absorption coefficient according to a substance contained in the subject based on initial values of the thickness information and the composition information, calculate new thickness information and new composition information based on the acquired absorption coefficient, acquire a new absorption coefficient based on the new thickness information and the new composition information, and repeat calculation of newer thickness information and newer composition information based on the new absorption coefficient and acquisition of a newer absorption coefficient based on the newer thickness information and the newer composition information to calculate the thickness information and the composition information and acquire the absorption coefficient.

In the energy subtraction processing apparatus according to the invention, in a case where the subject includes a contrast medium, the subject information acquisition unit may calculate the subject information by correcting a region of the contrast medium in the two radiographic images.

The energy subtraction processing apparatus according to the invention may further comprise a correction unit that corrects the subtraction image using the thickness information.

An energy subtraction processing method according to the invention comprises: acquiring two radiographic images with radiations transmitted through a subject and having different energy distributions; acquiring subject information including thickness information of the subject based on at least one of the two radiographic images; acquiring an absorption coefficient corresponding to the subject information with reference to a relationship between a thickness of the subject and an absorption coefficient of the radiation, which is calculated in advance according to the energy distribution and a substance forming the subject; calculating, based on the acquired absorption coefficient, a weighting coefficient in a case of performing weighting subtraction between corresponding pixels of the two radiographic images; and generating a subtraction image, in which a specific structure of the subject has been extracted, by performing weighting subtraction between the corresponding pixels of the two radiographic images using the weighting coefficient.

In the energy subtraction processing method according to the invention, the subject information may be acquired by analyzing at least one of the two radiographic images.

In the energy subtraction processing method according to the invention, the subject information may be acquired based on a radiographic image acquired with radiation having a low energy distribution between the two radiographic images.

In the energy subtraction processing method according to the invention, composition information of the subject may be further acquired as the subject information.

In the energy subtraction processing method according to the invention, the subject may be a breast, the thickness information may be a thickness of the breast, and the composition information may be a mammary gland content rate.

In the energy subtraction processing method according to the invention, the thickness information and the composition information may be calculated based on the two radiographic images, a tube voltage at the time of imaging, and the relationship between the thickness of the subject and the absorption coefficient of the radiation.

In the energy subtraction processing method according to the invention, an absorption coefficient according to a substance contained in the subject may be acquired based on initial values of the thickness information and the composition information, new thickness information and new composition information may be calculated based on the acquired absorption coefficient, a new absorption coefficient may be acquired based on the new thickness information and the new composition information, and calculation of newer thickness information and newer composition information based on the new absorption coefficient and acquisition of a newer absorption coefficient based on the newer thickness information and the newer composition information may be repeated to calculate the thickness information and the composition information and acquire the absorption coefficient.

In the energy subtraction processing method according to the invention, in a case where the subject includes a contrast medium, the subject information may be calculated by correcting a region of the contrast medium in the two radiographic images.

The energy subtraction processing method according to the invention may further comprise correcting the subtraction image using the thickness information.

In addition, a non-transitory computer readable recording medium storing a program causing a computer to execute the energy subtraction processing method according to the invention may be provided.

According to the invention, the subject information including the thickness information of the subject is acquired, and the absorption coefficient corresponding to the subject information is acquired with reference to the relationship between the thickness of the subject and the absorption coefficient of radiation, which is calculated in advance according to the energy distribution and the substance forming the subject. Then, the weighting coefficient at the time of performing weighting subtraction between corresponding pixels of the two radiographic images is calculated based on the acquired absorption coefficient, and the weighting subtraction between the corresponding pixels of the two radiographic images is performed using the weighting coefficient. As a result, a subtraction image is acquired. In this manner, by acquiring the appropriate absorption coefficient corresponding to the subject information with reference to the relationship between the thickness of the subject and the absorption coefficient of radiation, which is calculated in advance according to the energy distribution and the substance forming the subject, it is possible to accurately calculate the weighting coefficient. Therefore, it is possible to accurately extract a specific structure of the subject in the subtraction image. As a result, it is possible to generate a high-quality subtraction image having no artifacts.

DESCRIPTION OF THE PREFERRED EMBODIMENTS

Figure 1:
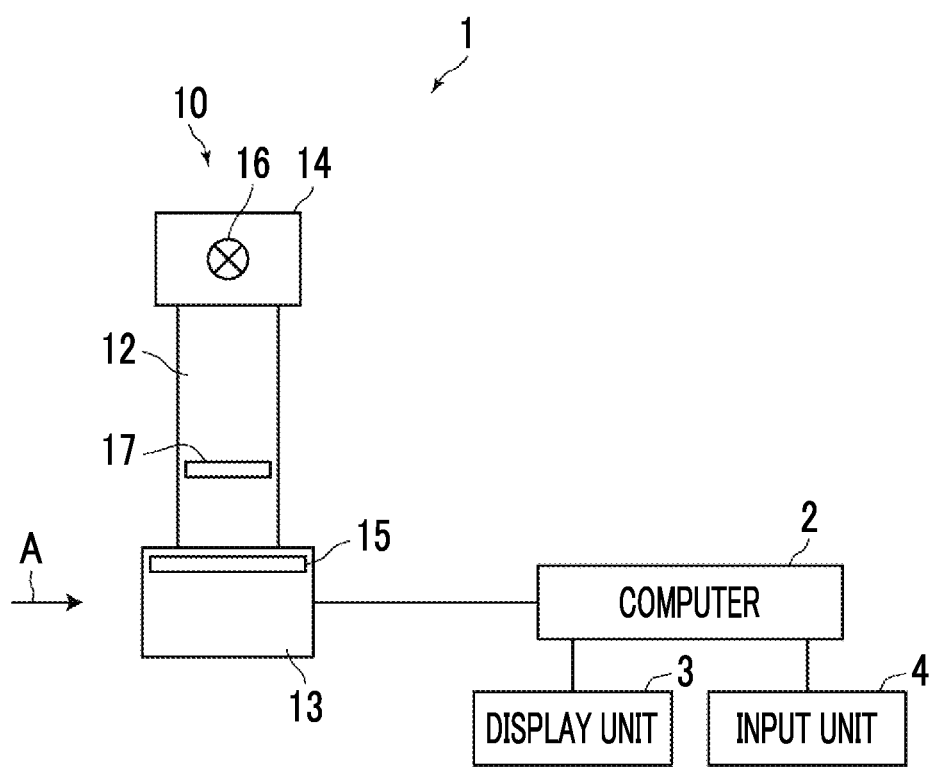
FIG. 1 is a view showing the schematic configuration of a radiographic image capturing apparatus to which an energy subtraction processing apparatus according to a first embodiment of the present invention is applied.
Figure 2:
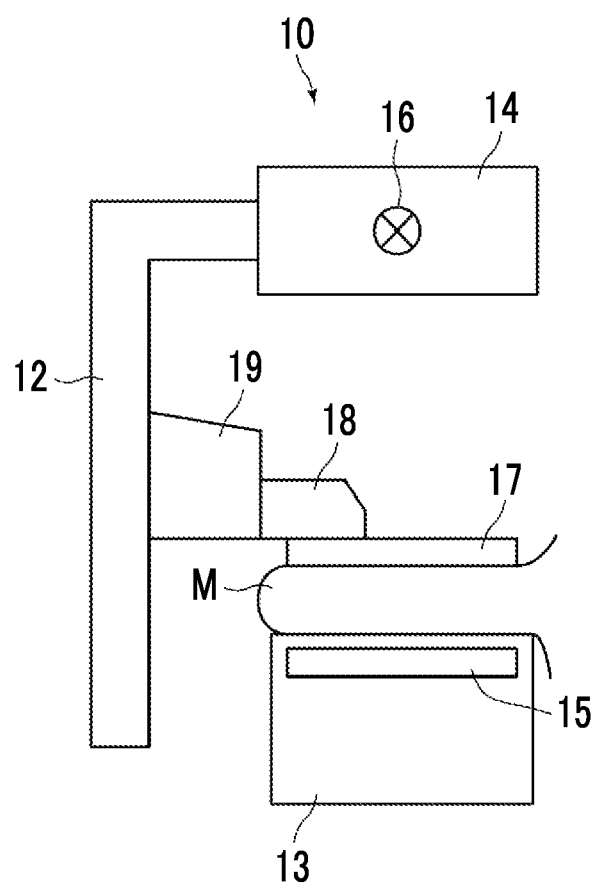
FIG. 2 is a diagram of the radiographic image capturing apparatus as viewed from the direction of arrow A in FIG. 1.

Hereinafter, embodiments of the invention will be described with reference to the accompanying diagrams. FIG. 1 is a schematic configuration diagram of a radiographic image capturing apparatus to which an energy subtraction processing apparatus according to a first embodiment of the invention is applied, and FIG. 2 is a diagram of the radiographic image capturing apparatus as viewed from the direction of arrow A in FIG. 1. A radiographic image capturing apparatus 1 is a mammography apparatus that captures an image of a breast M that is a subject. In the present embodiment, in order to generate an energy subtraction image (hereinafter, simply referred to as a subtraction image) by performing energy subtraction imaging of the breast M, radiation of different energy is emitted to the breast M, which is a subject, to acquire a low voltage image based on low energy radiation and a high voltage image based on high energy radiation. As shown in FIG. 1, the radiographic image capturing apparatus 1 includes an imaging unit 10, a computer 2 connected to the imaging unit 10, and a display unit 3 and an input unit 4 connected to the computer 2.

The imaging unit 10 includes an arm unit 12. An imaging table 13 is attached to one end portion of the arm unit 12, and an irradiation unit 14 is attached to the other end portion so as to face the imaging table 13.

A radiation detector 15, such as a flat panel detector, is provided inside the imaging table 13. In addition, a circuit board on which a charge amplifier for converting a charge signal read from the radiation detector 15 into a voltage signal, a correlated double sampling circuit for sampling a voltage signal output from the charge amplifier, an AD conversion unit for converting a voltage signal into a digital signal, and the like are provided inside the imaging table 13.

The radiation detector 15 can perform recording and reading of a radiographic image repeatedly. A so-called direct type radiation detector that generates an electric charge by direct reception of radiation may be used, or a so-called indirect type radiation detector that converts radiation into visible light and then converts the visible light into a charge signal may be used. As a method of reading a radiographic image signal, it is desirable to use a so-called TFT reading method in which a radiographic image signal is read by ON and OFF of a thin film transistor (TFT) switch or a so-called optical reading method in which a radiographic image signal is read by emission of reading light. However, other methods may also be used without being limited to the above methods.

An X-ray source 16, which is a radiation source, is housed inside the irradiation unit 14. The timing of emission of X-rays, which are radiations from the X-ray source 16, and X-ray generation conditions in the X-ray source 16, that is, imaging conditions such as a tube voltage and irradiation time are controlled by the computer 2.

A compression plate 17 disposed above the imaging table 13 to compress the breast M, a support unit 18 for supporting the compression plate 17, and a moving mechanism 19 for moving the support unit 20 in the vertical direction in FIGS. 1 and 2 are provided at the arm unit 12. Information of the distance between the compression plate 17 and the imaging table 13, that is, information of the height of the compression plate 17, is input to the computer 2.

The display unit 3 is a display device, such as a cathode ray tube (CRT) or a liquid crystal monitor, and displays a subtraction image obtained as will be described later, a message required for the operation, and the like. The display unit 3 may include a speaker to output sound.

The input unit 4 is a keyboard, a mouse, or a touch panel type input device, and receives an operation on the radiographic image capturing apparatus 1 by the operator. In addition, the input unit 4 receives an input of various kinds of information, such as imaging conditions, and an instruction to modify information, which is required to perform energy subtraction imaging. In the present embodiment, each unit of the radiographic image capturing apparatus 1 operates according to the information input from the input unit 4 by the operator.

An energy subtraction processing program is installed on the computer 2. In the present embodiment, the computer may be a workstation or a personal computer that is directly operated by the operator, or may be a server computer connected to these through a network. The energy subtraction processing program is distributed by being recorded on a recording medium, such as a digital versatile disc (DVD) and a compact disc read only memory (CD-ROM), and is installed on the computer from the recording medium. Alternatively, the energy subtraction processing program is stored in a storage device of a server computer connected to the network or in a network storage so as to be accessible from the outside, and is downloaded and installed on the computer as necessary.

Figure 3:
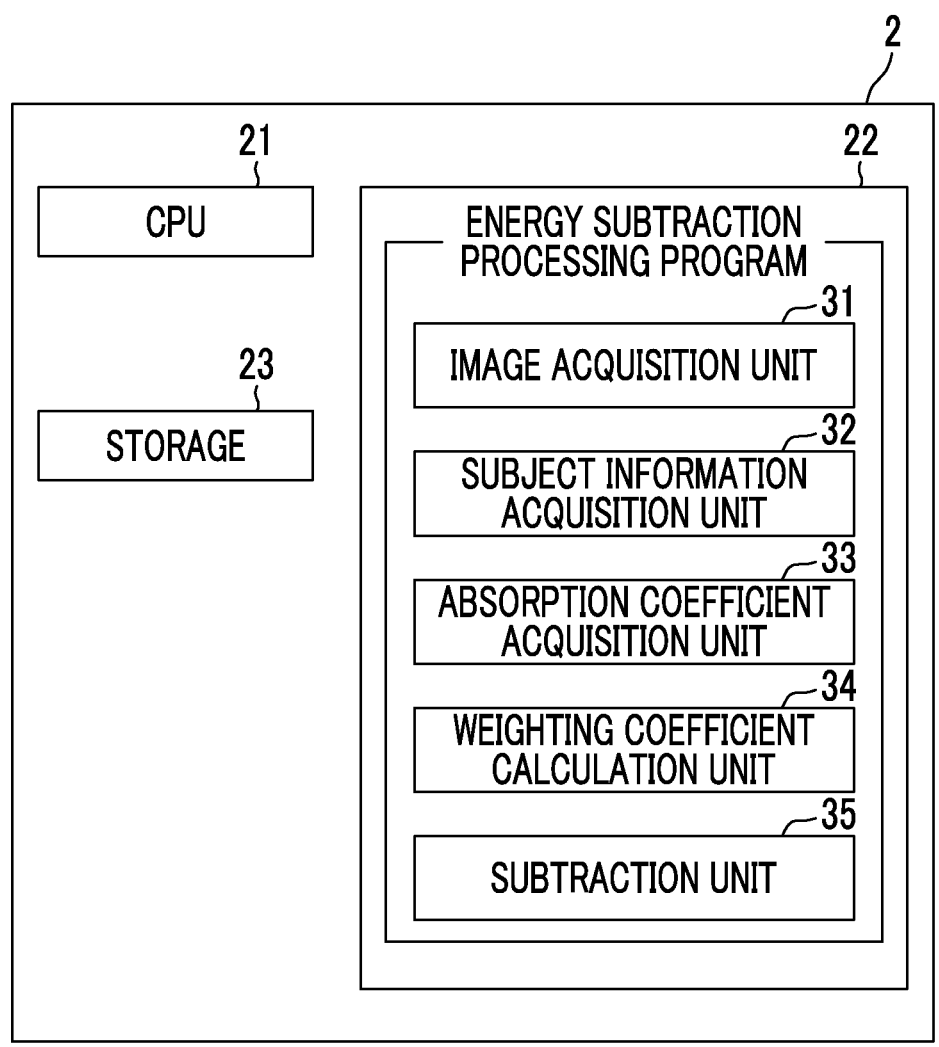
FIG. 3 is a diagram showing the schematic configuration of the energy subtraction processing apparatus according to the first embodiment.

FIG. 3 is a diagram showing the schematic configuration of an energy subtraction processing apparatus realized by installing an energy subtraction processing program in the computer 2. As shown in FIG. 3, the energy subtraction processing apparatus includes a central processing unit (CPU) 21, a memory 22, and a storage 23 as the configuration of a standard computer.

The storage 23 is a storage device, such as a hard disk or a solid state drive (SSD), and stores various kinds of information including a program for driving each unit of the radiographic image capturing apparatus 1 and an energy subtraction processing program. A low voltage image and a high voltage image acquired by energy subtraction imaging and a subtraction image generated as will be described later are also stored. Various tables to be described later are also stored in the storage 23.

The memory 22 temporarily stores programs and the like stored in the storage 23 so that the CPU 21 executes various kinds of processing. As processing to be executed by the CPU 21, the energy subtraction processing program defines: image acquisition processing for acquiring two radiographic images of a low voltage image and a high voltage image by causing the radiographic image capturing apparatus 1 to perform energy subtraction imaging; subject information acquisition processing for acquiring subject information including the thickness information of the breast M, which is a subject, based on at least one of the low voltage image or the high voltage image; absorption coefficient acquisition processing for acquiring an absorption coefficient corresponding to the subject information with reference to the relationship between the thickness of the breast M and the X-ray absorption coefficient and the X-ray energy distribution in the case of acquiring the low voltage image and the high voltage image, which is calculated in advance according to the substance forming the breast M; weighting coefficient calculation processing for calculating, based on the acquired absorption coefficient, a weighting coefficient in the case of performing weighting subtraction between corresponding pixels of the low voltage image and the high voltage image; and subtraction processing for generating a subtraction image, in which a specific structure of the breast M has been extracted, by performing weighting subtraction between the corresponding pixels of the two radiographic images using the weighting coefficient.

Then, the CPU 21 executes these processes according to the energy subtraction processing program, so that the computer 2 functions as an image acquisition unit 31, a subject information acquisition unit 32, an absorption coefficient acquisition unit 33, a weighting coefficient calculation unit 34, and a subtraction unit 35. The computer 2 may include a processor or a processing circuit that performs image acquisition processing, subject information acquisition processing, absorption coefficient acquisition processing, weighting coefficient calculation processing, and subtraction processing.

The image acquisition unit 31 controls the irradiation unit 14 to emit two types of radiation having different energy distributions, thereby performing energy subtraction imaging according to a so-called two-shot method. Specifically, low voltage imaging using X-rays of relatively low energy and high voltage imaging using X-rays of relatively high energy are performed. In the low voltage imaging, the X-ray source 16 is driven under the imaging conditions in which X-rays of relatively low energy are emitted (for example, a tube voltage of the X-ray source 16 is set to 26 kV) so that the X-rays are emitted to the breast M, and X-rays transmitted through the breast M are detected by the radiation detector 15, thereby acquiring a low voltage image GL. In the high voltage imaging, the X-ray source 16 is driven under the imaging conditions in which X-rays of relatively high energy are emitted (for example, a tube voltage of the X-ray source 16 is set to 45 kV) so that the X-rays are emitted to the breast M, and X-rays transmitted through the breast M are detected by the radiation detector 15, thereby acquiring a high voltage image GH. Alternatively, the low voltage image GL and the high voltage image GH may be acquired by using a one-shot method in which two radiation detectors 15 are disposed so as to overlap each other inside the imaging table 13 and X-rays transmitted through the breast M are simultaneously emitted to the two radiation detectors 15 overlapping each other so that X-rays having different energy distributions are emitted to the two radiation detectors 15.

Figure 4:
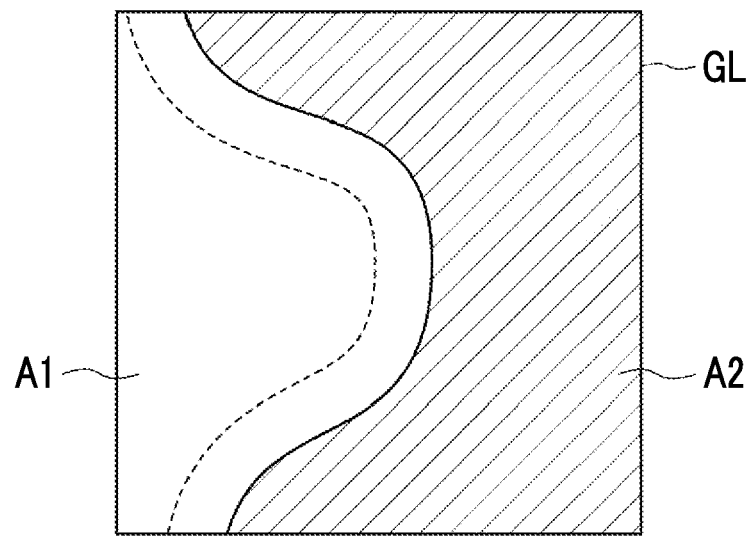
FIG. 4 is a diagram illustrating the detection of a breast region.

The subject information acquisition unit 32 acquires subject information including the thickness information of the breast M based on at least one of the low voltage image GL or the high voltage image GH. In the present embodiment, the thickness information of the breast M and the mammary gland content rate in the breast M are acquired as the subject information based on the low voltage image GL. The mammary gland content rate corresponds to the composition information of the subject. First, acquisition of the thickness information of the breast M will be described. The subject information acquisition unit 32 detects a region of the breast M from the low voltage image GL first. FIG. 4 is a diagram illustrating the detection of the region of the breast M. As shown in FIG. 4, the low voltage image GL includes a region A1 of the breast M and a blank region A2 which is a region where X-rays are directly emitted to the radiation detector 15. Here, the blank region A2 has a higher density than the region A1 of the breast. Therefore, by performing threshold processing on the low voltage image GL, the region A1 of the breast M can be detected.

Figure 5:
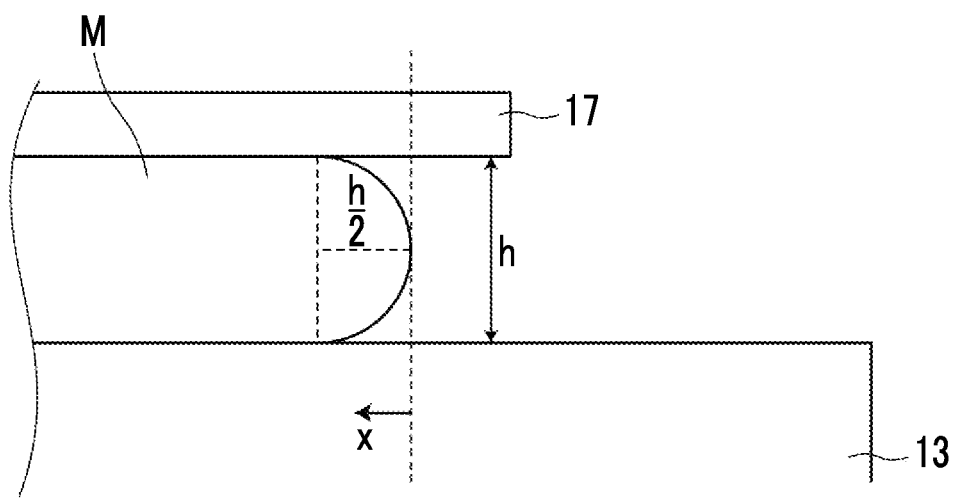
FIG. 5 is a diagram showing the breast interposed between a compression plate and an imaging table.

Here, at the time of imaging, the breast M is interposed between the imaging table 13 and the compression plate 17 as shown in FIG. 5. Therefore, in the vicinity of a boundary between the region A1 of the breast and the blank region A2 (hereinafter, the boundary is referred to as a skin line) in the image acquired by imaging, the breast M is in contact with neither the imaging table 13 nor the compression plate 17. The subject information acquisition unit 32 acquires information of the height of the compression plate 17 from the imaging unit 10. Here, in the vicinity of the skin line of the breast M, it is assumed that the shape of the breast M is semicircular in cross section. Assuming that the height of the compression plate 17 is h, in the region A1 of the breast M acquired from the low voltage image GL, the height h of the compression plate 17 is acquired as the thickness information of the breast M in a region exceeding h/2 from the skin line. A position at the distance h/2 from the skin line is shown by a broken line. On the other hand, in a region from the skin line to the distance h/2, the thickness information of the breast M is acquired by calculating a thickness R according to the following Equation (1) with the distance from the skin line being x.

$$R = (0.5h - x)\sqrt{\left(\frac{0.5h}{0.5h - x}\right)^2 - 1} \qquad (1)$$

Next, acquisition of the mammary gland content rate as composition information will be described. In the present embodiment, the subject information acquisition unit 32 calculates the mammary gland content rate from the low voltage image GL using the method disclosed in JP2010-253245A, for example. In the method disclosed in JP2010-253245A, the mammary gland content rate is calculated from the low voltage image GL as follows. First, in the low voltage image GL, a fat image that is an image having a pixel value in a case where all the mammary gland tissues of the breast M are replaced with adipose tissues is generated. Then, based on the low voltage image GL, the fat image, and the pixel value of the blank region A2 in the low voltage image GL and a ratio between the average attenuation coefficient of the mammary gland and the average attenuation coefficient of fat stored in the storage 23, the mammary gland content rate is calculated for each pixel of the low voltage image GL.

Figure 6:
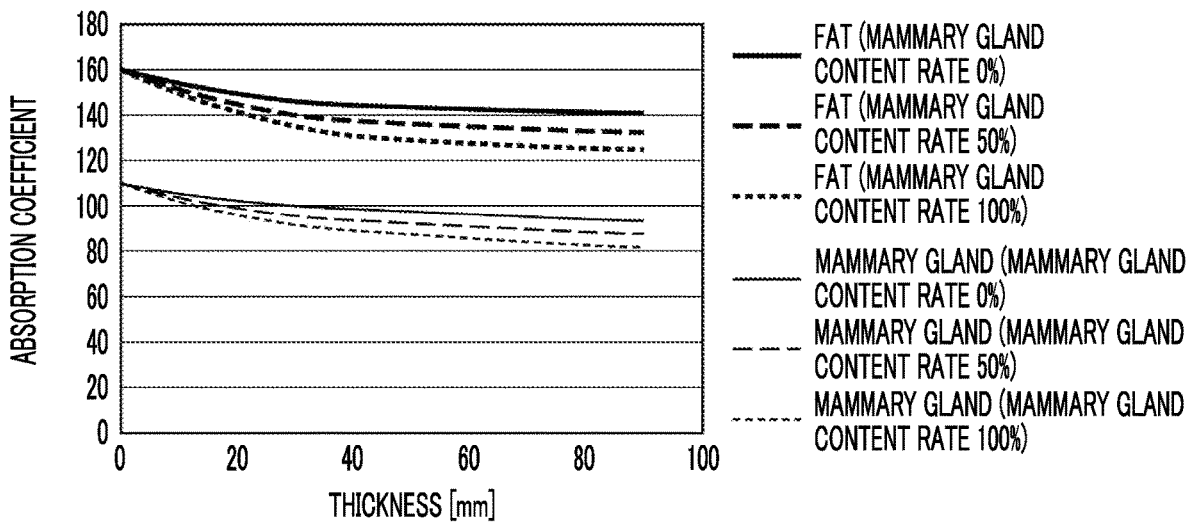
FIG. 6 is a diagram showing the relationship between the breast thickness and an X-ray absorption coefficient calculated in advance according to the substance forming the breast (low energy).
Figure 7:
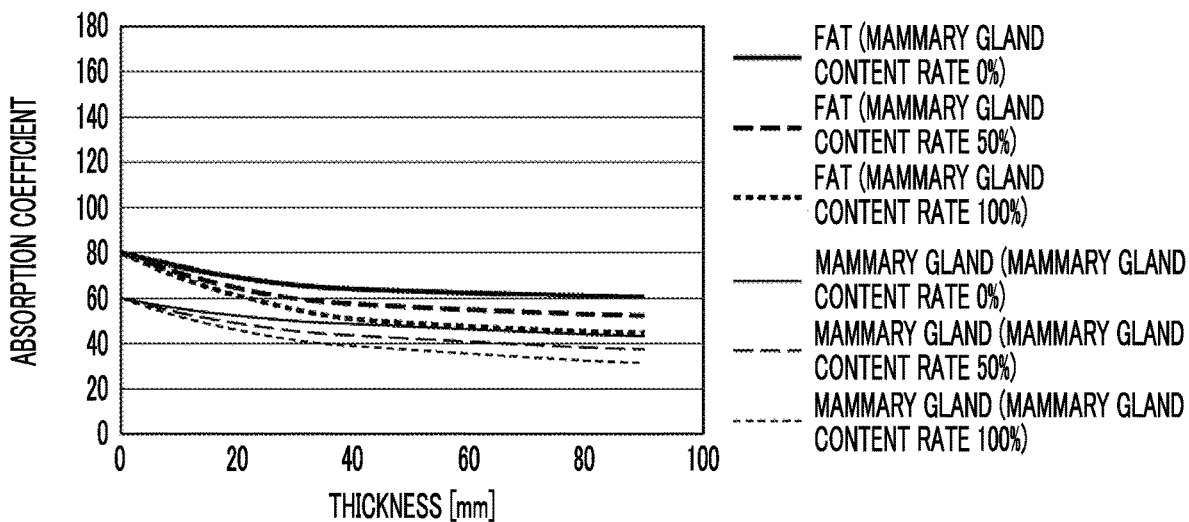
FIG. 7 is a diagram showing the relationship between the breast thickness and an X-ray absorption coefficient calculated in advance according to the substance forming the breast (high energy).

The absorption coefficient acquisition unit 33 acquires an absorption coefficient corresponding to the subject information with reference to the relationship between the thickness of the breast M and the X-ray absorption coefficient, which is calculated in advance according to the energy distribution and the substance forming the breast M. In the present embodiment, the relationship between the thickness of the breast M and the X-ray absorption coefficient, which is calculated in advance according to the energy distribution and the substance forming the breast M, is stored in the storage 23. FIGS. 6 and 7 are diagrams showing the relationship between the thickness of the breast M and the X-ray absorption coefficient, which is calculated in advance according to the substance forming the breast M. FIG. 6 shows an absorption coefficient with respect to low energy X-rays as the energy distribution, and FIG. 7 shows an absorption coefficient with respect to high energy X-rays as the energy distribution. As shown in FIGS. 6 and 7, the relationship between the thickness of the breast M and the absorption coefficient is stored in the storage 23 for each of fat and mammary gland forming the breast M. Here, the absorption coefficient of the substance is determined depending on the energy of X-rays. In a process in which X-rays are transmitted through the subject, the low energy component of the X-rays is absorbed by the subject, and beam hardening that causes increasing ratio of high energy X-rays occurs. Therefore, as shown in FIGS. 6 and 7, the absorption coefficient decreases as the thickness of the breast M increases. The beam hardening differs depending on the composition of the subject. In a case where the subject is the breast M, as shown in FIGS. 6 and 7, the absorption coefficient decreases as the mammary gland content rate increases. In addition, the absorption coefficient decreases as the energy of X-rays increases.

Based on the relationship shown in FIGS. 6 and 7 and the subject information acquired by the subject information acquisition unit 32, the absorption coefficient acquisition unit 33 acquires the absorption coefficients of fat and mammary gland corresponding to the energy of X-rays, the thickness of the breast M, and the mammary gland content rate. Specifically, an absorption coefficient $\mu_g^L$ of mammary gland and an absorption coefficient $\mu_a^L$ of fat for low energy X-rays, and an absorption coefficient $\mu_g^H$ of mammary gland and an absorption coefficient $\mu_a^H$ of fat for high energy X-rays are acquired.

FIGS. 6 and 7 show the relationship between the thickness and the absorption coefficient in a case where the mammary gland content rate is 0%, 50%, and 100%. However, in a case where the mammary gland content rate is an intermediate value between these values, the relationship may be acquired by calculating the absorption coefficient by interpolation calculation.

Based on the absorption coefficient acquired by the absorption coefficient acquisition unit 33, the weighting coefficient calculation unit 34 calculates a weighting coefficient at the time of performing energy subtraction processing.

The subtraction unit 35 generates a subtraction image, in which the mammary glands of the breast M have been extracted, by performing weighting subtraction processing between corresponding pixels of the low voltage image GL and the high voltage image GH using the weighting coefficient calculated by the weighting coefficient calculation unit 34.

In a case where the subtraction unit 35 calculates a subtraction image Gs according to the following Equation (2), the weighting coefficient calculation unit 34 calculates a weighting coefficient α according to the following Equation (3). The subtraction unit 35 generates the subtraction image Gs according to the following Equation (3).

$$Gs = \alpha \cdot GH - GL \qquad (2)$$

$$\alpha = (\mu_g^H - \mu_a^H)/(\mu_g^L - \mu_a^L) \qquad (3)$$

Figure 8:
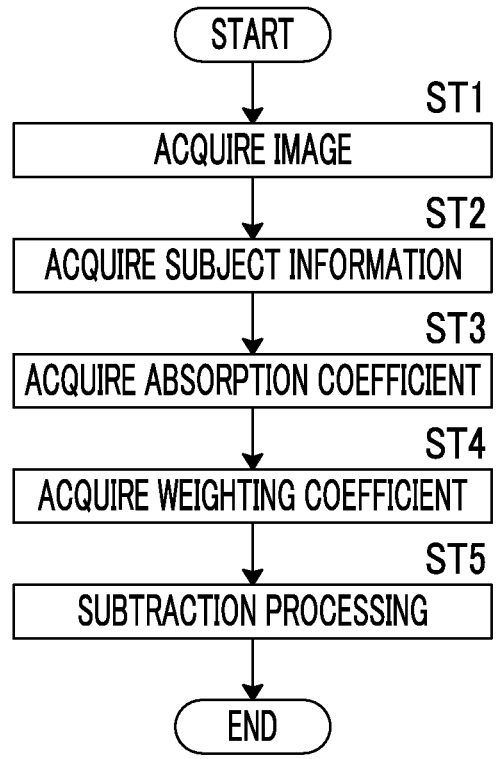
FIG. 8 is a flowchart showing the process performed in the first embodiment.

Next, the process performed in the first embodiment will be described. FIG. 8 is a flowchart showing the process performed in the first embodiment. In a case where the input unit 4 receives an operator's instruction to start the process, energy subtraction imaging is performed so that the image acquisition unit 31 acquires the low voltage image GL and the high voltage image GH (step ST1). Then, the subject information acquisition unit 32 acquires the thickness information of the breast M and the mammary gland content rate as the subject information based on the low voltage image GL (step ST2). Then, the absorption coefficient acquisition unit 33 acquires an absorption coefficient corresponding to the subject information with reference to the relationship between the thickness of the breast M and the X-ray absorption coefficient, which is calculated in advance according to the energy distribution and the substance forming the breast M (step ST3).

Then, based on the absorption coefficient acquired by the absorption coefficient acquisition unit 33, the weighting coefficient calculation unit 34 calculates a weighting coefficient at the time of performing energy subtraction processing (step ST4). Then, the subtraction unit 35 generates the subtraction image Gs, in which the mammary glands of the breast M have been extracted, by performing weighting subtraction processing between corresponding pixels of the low voltage image GL and the high voltage image GH using the weighting coefficient calculated by the weighting coefficient calculation unit 34 (step ST5), and the process is ended. The subtraction image Gs is displayed on the display unit 3.

As described above, in the first embodiment, the subject information including the thickness information of the breast M and the mammary gland content rate is acquired, and the absorption coefficient corresponding to the subject information is acquired with reference to the relationship between the thickness of the subject and the X-ray absorption coefficient, which is calculated in advance according to the energy distribution and the substance forming the subject. Then, the weighting coefficient at the time of performing weighting subtraction between corresponding pixels of the low voltage image GL and the high voltage image GH is calculated based on the acquired absorption coefficient, and the weighting subtraction between the corresponding pixels of the low voltage image GL and the high voltage image GH is performed using the weighting coefficient. As a result, the subtraction image Gs is acquired. In this manner, by acquiring the appropriate absorption coefficient corresponding to the subject information with reference to the relationship between the thickness of the breast M and the X-ray absorption coefficient, which is calculated in advance according to the energy distribution and the substance forming the subject, it is possible to accurately calculate the weighting coefficient. Therefore, it is possible to accurately extract the mammary gland of the breast M in the subtraction image Gs. As a result, it is possible to generate the high-quality subtraction image Gs.

The low voltage image GL has a higher contrast than the high voltage image GH. Therefore, by acquiring the subject information based on the low voltage image GL, it is possible to accurately acquire the subject information.

Next, a second embodiment of the invention will be described. The configuration of an energy subtraction processing apparatus according to the second embodiment is the same as the configuration of the energy subtraction processing apparatus according to the first embodiment, and only the processing to be performed is different. Accordingly, the detailed explanation thereof will be omitted herein. The energy subtraction processing apparatus according to the second embodiment is different from the energy subtraction processing apparatus according to the first embodiment in that the subject information acquisition unit 32 calculates the thickness information of the breast M and the mammary gland content rate based on each pixel value of the low voltage image GL, each pixel value of the high voltage image GH, and the relationship between the absorption coefficient and the tube voltage at the time of imaging.

Figure 9:
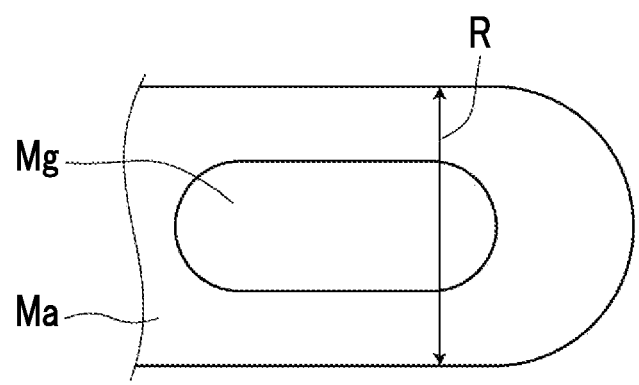
FIG. 9 is a diagram showing a cross section of a compressed breast.

FIG. 9 is a conceptual diagram illustrating processing of the second embodiment. FIG. 9 is a conceptual diagram showing a cross section of the breast M in a state in which the breast M is compressed by the compression plate 17. In addition, FIG. 9 schematically shows a state in which fat Ma and mammary gland Mg are contained in the breast M. R in FIG. 9 indicates the thickness of the breast M. As shown in FIG. 9, in the breast M including the fat Ma and the mammary gland Mg, the dose reaching the radiation detector 15 is expressed by the following Equation (4).

$$N \approx \phi_0(E_0) e^{-\mu_g(E_0) r_g - \mu_a(E_0) r_a} \tag{4}$$

Here, N is a dose at the time of acquiring a radiographic image, $\phi_0$ is a function indicating the dose and the sensitivity of a radiation detector, $E_0$ is a tube voltage of the X-ray source 16, $r_a$ is a fat thickness, $r_g$ is a mammary gland thickness, $\mu_a$ is an X-ray absorption coefficient of fat, and $\mu_g$ is an X-ray absorption coefficient of mammary gland.

Assuming that the tube voltages of the X-ray source 16 at the time of acquiring the low voltage image GL and the high voltage image GH are $E_L$ and $E_H$ and the doses reaching the radiation detector 15 at the time of acquiring the low voltage image GL and the high voltage image GH are $N^L$ and $N^H$, the doses $N^L$ and $N^H$ are calculated according to Equation (4) for the low voltage image GL and the high voltage image GH, respectively. By log converting the result, the following Equations (5) and (6) are obtained. $C_1$ and $C_2$ are constants.

$$\mathrm{LOG}(N^H) = \mu_g^H(E_H) r_g - \mu_a^H(E_H) r_a + C_1 \tag{5}$$

$$\mathrm{LOG}(N^L) = \mu_g^L(E_L) r_g - \mu_a^L(E_L) r_a + C_2 \tag{6}$$

Here, $N^L$ is a dose at the time of acquiring the low voltage image GL, $N^H$ is a dose at the time of acquiring the high voltage image GH, $E_L$ is a tube voltage of the X-ray source 16 at the time of low voltage imaging, $E_H$ is a tube voltage of the X-ray source 16 at the time of high voltage imaging, $\mu_a^L$ is an absorption coefficient of fat for low energy X-rays, $\mu_g^L$ is an absorption coefficient of mammary gland for low energy X-rays, $\mu_a^H$ is an absorption coefficient of fat for high energy X-rays, and $\mu_g^H$ is an absorption coefficient of mammary gland for high energy X-rays.

In this case, since the thickness R of the breast M is $R = r_a + r_g$, the thickness R is calculated according to the following Equation (7). $C_1$, $C_2$, and $C_3$ are constants determined according to the imaging conditions and the sensitivity of the radiation detector 15.

$$R = \beta^*(\alpha^* \mathrm{LOG}(N^H) - \mathrm{LOG}(N^L)) + C_3 \tag{7}$$

Here, $$\beta = \left( \frac{\mu_g^H(E_H) - \mu_a^H(E_H)}{(\mu_g^L(E_L) - \mu_a^L(E_L)) \mu_a^L(E_L) - (\mu_g^H(E_H) - \mu_a^H(E_H)) \mu_g^H(E_H)} \right),$$

$$\alpha = \frac{\mu_g^L(E_L) - \mu_a^L(E_L)}{\mu_g^H(E_H) - \mu_a^H(E_H)}$$

In the second embodiment, first, the subject information acquisition unit 32 regards the height of the compression plate 17 as the thickness of the breast M, and acquires the absorption coefficient $\mu_g^L$ of mammary gland and the absorption coefficient $\mu_a^L$ of fat for low energy X-rays and the absorption coefficient $\mu_g^H$ of mammary gland and the absorption coefficient $\mu_a^H$ of fat for high energy X-rays with reference to the relationship shown in FIGS. 6 and 7 used in the first embodiment. The mammary gland content rate at the time of acquiring the absorption coefficient is 50%. Based on the signal values at the respective pixel positions of the low voltage image GL and the high voltage image GH, the subject information acquisition unit 32 acquires the dose $N^L$ at the time of acquiring the low voltage image GL and the dose $N^H$ at the time of acquiring the high voltage image GH. The dose is acquired for each pixel position. Then, the acquired absorption coefficients and doses are substituted into Equations (5) and (6). Then, by solving Equations (5) and (6) for $r_a$ and $r_g$, the thickness $r_a$ of fat and the thickness $r_g$ of mammary gland are calculated for each pixel position. Then, by substituting the thickness $r_a$ of fat and the thickness $r_g$ of the mammary gland into Equation (7), the thickness R of the breast M at each pixel position is calculated.

Here, since the thickness R of the breast M is $R = r_a + r_g$, $r_g = R - r_a$. Therefore, using the calculated thickness R of the breast M, the thickness $r_g$ of the mammary gland can be calculated according to Equation (6) to the following Equation (8).

$$r_g = \frac{1}{\mu_g^L(E_L) - \mu_a^L(E_L)}(C_2 - \text{LOG}(N^L) - \mu_a^L(E_L) * R) \quad (8)$$

Accordingly, the mammary gland content rate can be calculated by $r_g/R$. As described above, in the second embodiment, the subject information acquisition unit 32 acquires the subject information by calculating the thickness R of the breast M and the mammary gland content rate.

Here, acquisition of an absorption coefficient, calculation of a weighting coefficient, and subtraction processing in the second embodiment are performed in the same manner as in the first embodiment.

Figure 10:
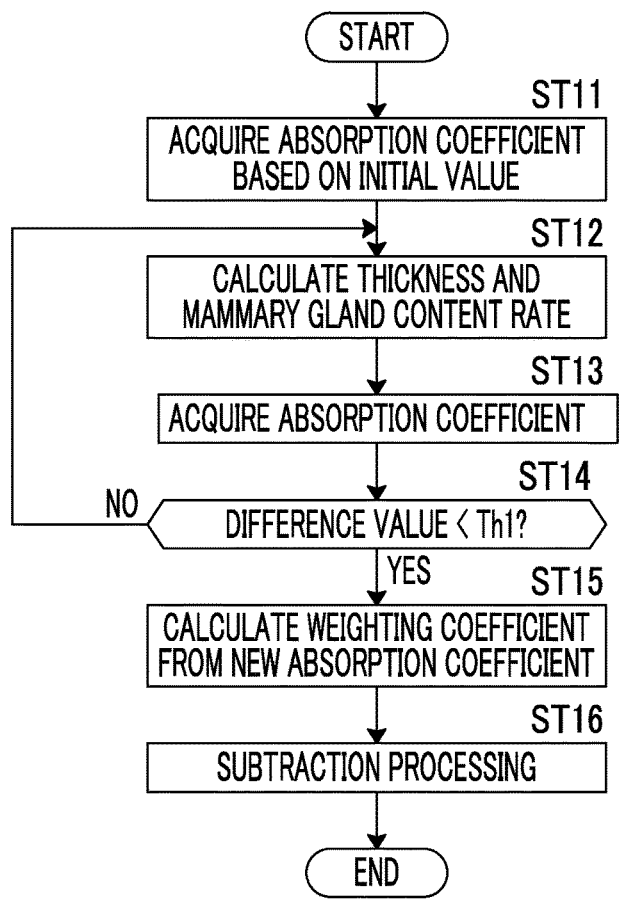
FIG. 10 is a flowchart showing the process performed in a third embodiment.

In the second embodiment described above, in order to acquire the more accurate thickness R of the breast M and the more accurate mammary gland content rate, which are suitable for the subject, repetitive calculation may be performed. Hereinafter, this will be described as a third embodiment. FIG. 10 is a flowchart of repetitive calculation in the third embodiment.

In the third embodiment, as in the second embodiment described above, first, the subject information acquisition unit 32 acquires an absorption coefficient with the initial value of the thickness R being the height of the compression plate 17 and the initial value of the mammary gland content rate being 50% (absorption coefficient acquisition using initial values: step ST11). Then, as in the second embodiment, the thickness R of the breast M and the mammary gland content rate are calculated as the subject information (step ST12). In the third embodiment, using the calculated thickness R and mammary gland content rate, the absorption coefficient is acquired with reference to the relationship shown in FIGS. 6 and 7 (step ST13). Then, the subject information acquisition unit 32 determines whether or not a difference value between the absorption coefficient acquired in step ST13 and the absorption coefficient acquired in the previous processing is less than a threshold value Th1 (step ST14). In the first processing, the difference value is a difference between the absorption coefficient acquired in step ST13 and the absorption coefficient acquired using the initial values of the thickness R and the mammary gland content rate.

Here, the absorption coefficient $\mu_a^L$ of fat for low energy X-rays, the absorption coefficient $\mu_g^L$ of mammary gland for low energy X-rays, the absorption coefficient $\mu_a^H$ of fat for high energy X-rays, and the absorption coefficient $\mu_g^H$ of mammary gland for high energy X-rays are acquired as absorption coefficients. Therefore, in the processing of step ST13, it is determined whether or not difference values for all the four absorption coefficients are less than the threshold value Th1. The threshold value Th1 may be set for each absorption coefficient. Here, it is assumed that step ST14 is affirmed in a case where all the four difference values are less than the threshold value Th1.

In a case where step ST14 is denied, the subject information acquisition unit 32 returns to step ST12 to calculate a new thickness R and a new mammary gland content rate and acquire a new absorption coefficient using the thickness R and the mammary gland content rate calculated in step ST12 and the absorption coefficient acquired in step ST13. Then, the processing of steps ST12 and ST13 is repeated until step ST14 is affirmed. In a case where step ST14 is affirmed, the weighting coefficient calculation unit 34 calculates a weighting coefficient from the absorption coefficients acquired by the absorption coefficient acquisition unit 33 (step ST15), and the subtraction unit 35 generates the subtraction image Gs, in which the mammary glands of the breast M have been extracted, by performing weighting subtraction processing between corresponding pixels of the low voltage image GL and the high voltage image GH using the weighting coefficient calculated by the weighting coefficient calculation unit 34 (step ST16). Then, the process is ended. The subtraction image Gs is displayed on the display unit 3.

As described above, in the third embodiment, since the thickness R and the mammary gland content rate are calculated by repetitive calculation and the absorption coefficient is acquired, it is possible to acquire an absorption coefficient more suitable for the subject. Therefore, by calculating the weighting coefficient using the acquired absorption coefficients, it is possible to generate the subtraction image Gs with higher image quality in which the mammary glands have been accurately extracted.

Figure 11:
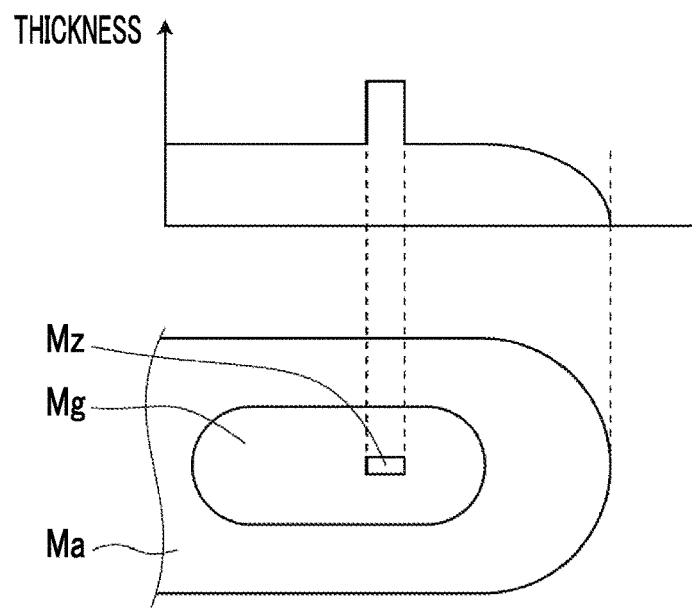
FIG. 11 is a diagram illustrating a thickness calculated in a case where a contrast medium is used.

In mammography, there is a case of generating a subtraction image in which a part of a blood vessel in a mammary gland has been extracted using a contrast medium. In the low voltage image GL and the high voltage image GH, the contrast medium appears as a region having a high density (low brightness). Therefore, in the case of calculating and acquiring the thickness R of the breast M as in the second and third embodiments, as shown in FIG. 11, the thickness of a portion of a contrast medium Mz becomes larger than the other portions. For this reason, it is preferable to correct the region of the contrast medium in the low voltage image GL and the high voltage image GH.

Specifically, a region of the breast M in the low voltage image GL and the high voltage image GH is detected, and a region having a high density in the region of the breast M is detected as a contrast medium region. Then, the low voltage image GL and the high voltage image GH are corrected by replacing pixel values in the contrast medium region with the surrounding pixel values. After correcting the low voltage image GL and the high voltage image GH as described above, subject information is acquired. Accordingly, since it is possible to calculate the weighting coefficient by acquiring the absorption coefficient without being affected by the contrast medium, it is possible to accurately calculate the subtraction image Gs.

At the time of imaging the breast M, as shown in FIG. 5, the vicinity of the skin line is not in close contact with the imaging table 13. For this reason, the thickness R of the breast M decreases in a region between the broken line and the skin line in FIG. 4. Therefore, in the subtraction image Gs, the density increases in the vicinity of the skin line of the breast M. For this reason, the density of the subtraction image Gs may be corrected using the thickness R of the breast M calculated according to the above Equation (7). Hereinafter, this will be described as a fourth embodiment.

Figure 12:
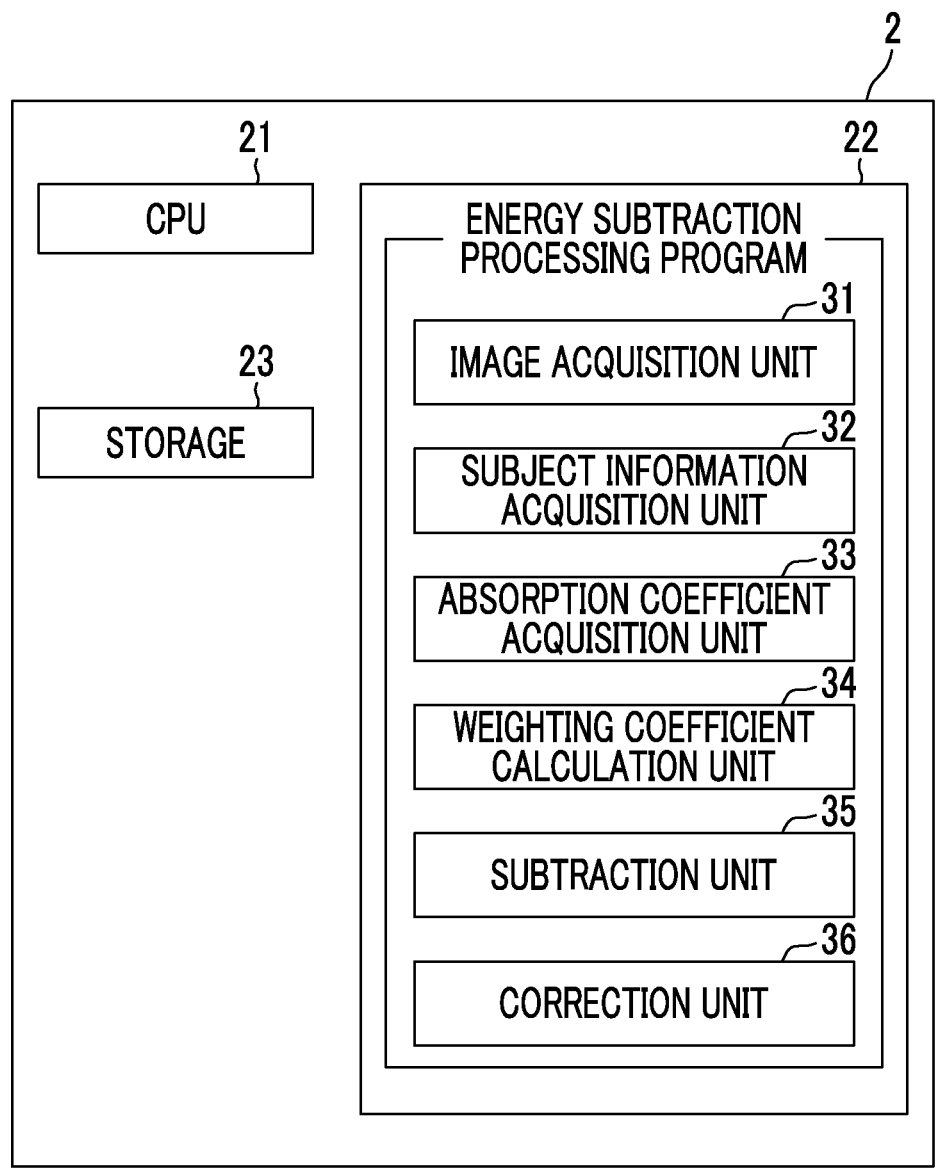
FIG. 12 is a diagram showing the schematic configuration of an energy subtraction processing apparatus according to a fourth embodiment.

FIG. 12 is a diagram showing the schematic configuration of an energy subtraction processing apparatus according to a fourth embodiment. In FIG. 12, the same components as in FIG. 3 are denoted by the same reference numbers, and the detailed explanation thereof will be omitted herein. The fourth embodiment is different from the first embodiment in that a correction unit 36 that corrects the subtraction image Gs using thickness information is further provided.

The correction unit 36 compares the thickness, which has been calculated according to Equation (7) by the subject information acquisition unit 32, for each pixel of the subtraction image Gs. Then, in a pixel having a smaller thickness than other pixels, correction is made so that the density of the pixel value is close to the densities of the other pixels. Therefore, in the corrected subtraction image Gs, the density in the vicinity of the skin line can be made to be the same as the densities in the other regions. As a result, it is possible to generate the subtraction image Gs with higher image quality.

In the above embodiment, the breast M is used as a subject, but the invention is not limited thereto. For example, a chest may be used as a subject. In this case, by preparing the relationship between the thickness of the subject and the X-ray absorption coefficient corresponding to the soft tissue and the bone tissue in the chest, it is possible to accurately calculate the weighting coefficient in the case of performing subtraction processing. Therefore, in the subtraction image, soft tissue or bone tissue can be accurately extracted.

Hereinafter, the effect of the present embodiment will be described.

A radiographic image acquired by the low energy radiation between two radiographic images acquired with radiations having different energy distributions has a higher contrast than a radiographic image acquired by the high energy radiation. Therefore, by acquiring the subject information based on the radiographic image acquired with the radiation having a low energy distribution between the two radiographic images, it is possible to accurately acquire the subject information.

In addition, since the composition information of the subject is acquired as the subject information, the weight coefficient can be calculated more accurately by acquiring an absorption coefficient more suitable for the subject according to the thickness information and the composition information of the subject. Therefore, it is possible to generate a subtraction image with higher image quality, in which a target structure has been accurately extracted.

In a case where the subject includes a contrast medium, by calculating the subject information by correcting the region of the contrast medium in the two radiographic images, it is possible to calculate the subject information excluding the effect of the contrast medium. Therefore, since it is possible to calculate the weighting coefficient by acquiring the absorption coefficient without being affected by the contrast medium, it is possible to generate a subtraction image with higher image quality.

By correcting the subtraction image using the thickness information, it is possible to generate a subtraction image with higher image quality.

EXPLANATION OF REFERENCES

1: radiographic image capturing apparatus
2: computer
3: display unit
4: input unit
10: imaging unit
12: arm unit
13: imaging table
14: irradiation unit
15: radiation detector
16: X-ray source
17: compression plate
18: support unit
19: moving mechanism
21: CPU
22: memory
23: storage
31: image acquisition unit
32: subject information acquisition unit
33: absorption coefficient acquisition unit
34: weighting coefficient calculation unit
35: subtraction unit
36: correction unit
A1: breast region
A2: blank region
M: breast
Ma: fat
Mg: mammary gland
R: height of compression plate
GL: low voltage image
GH: high voltage image
Gs: subtraction image

What is claimed is:

1. An energy subtraction processing apparatus, comprising:
a processor configured to execute:
an image acquisition unit that acquires two radiographic images with radiations transmitted through a breast and having different energy distributions;
a subject information acquisition unit that acquires thickness information of the breast based on at least one of the two radiographic images;
an absorption coefficient acquisition unit that acquires an absorption coefficient according to the thickness information of the breast;
a weighting coefficient calculation unit that calculates a weighting coefficient based on the acquired absorption coefficient; and
a subtraction unit that generates a subtraction image by performing weighting subtraction between corresponding pixels of the two radiographic images using the weighting coefficient,
wherein the subject information acquisition unit further acquires information of a mammary gland content rate of the breast,
the subject information acquisition unit calculates the thickness information of the breast and the information of the mammary gland content rate of the breast based on the two radiographic images and a tube voltage at the time of imaging,
the subject information acquisition unit and the absorption coefficient acquisition unit acquire an absorption coefficient according to a substance contained in the breast based on initial values of the thickness information of the breast and the information of the mammary gland content rate of the breast, calculate new thickness information of the breast and new information of the mammary gland content rate of the breast based on the acquired absorption coefficient, acquire a new absorption coefficient based on the new thickness information of the breast and the new information of the mammary gland content rate of the breast, and repeat calculation of newer thickness information of the breast and newer information of the mammary gland content rate of the breast based on the new absorption coefficient and acquisition of a newer absorption coefficient based on the newer thickness information of the breast and the newer information of the mammary gland content rate of the breast to calculate the thickness information of the breast and the information of the mammary gland content rate of the breast and acquire the absorption coefficient.

2. The energy subtraction processing apparatus according to claim 1,
wherein the subject information acquisition unit acquires the thickness information of the breast by analyzing at least one of the two radiographic images.

3. The energy subtraction processing apparatus according to claim 1,
wherein the subject information acquisition unit acquires the thickness information of the breast based on a radiographic image acquired with radiation having a low energy distribution between the two radiographic images.

4. The energy subtraction processing apparatus according to claim 2,
wherein the subject information acquisition unit acquires the thickness information of the breast based on a radiographic image acquired with radiation having a low energy distribution between the two radiographic images.

5. The energy subtraction processing apparatus according to claim 1,
wherein, in a case where the breast includes a contrast medium, the subject information acquisition unit calculates the thickness information of the breast by correcting a region of the contrast medium in the two radiographic images.

6. The energy subtraction processing apparatus according to claim 1, wherein the processor is configured to further execute:
a correction unit for correcting the subtraction image using the thickness information of the breast.

7. An energy subtraction processing method, comprising:
acquiring two radiographic images with radiations transmitted through a breast and having different energy distributions;
acquiring thickness information of the breast based on at least one of the two radiographic images;
acquiring an absorption coefficient according to the thickness information of the breast;
calculating a weighting coefficient based on the acquired absorption coefficient; and
generating a subtraction image by performing weighting subtraction between corresponding pixels of the two radiographic images using the weighting coefficient,
wherein information of a mammary gland content rate of the breast is further acquired,
the thickness information of the breast and the information of the mammary gland content rate of the breast are calculated based on the two radiographic images and a tube voltage at the time of imaging, an absorption coefficient according to a substance contained in the breast is acquired based on initial values of the thickness information of the breast and the information of the mammary gland content rate of the breast, new thickness information of the breast and new information of the mammary gland content rate of the breast are calculated based on the acquired absorption coefficient, a new absorption coefficient is acquired based on the new thickness information of the breast and the new information of the mammary gland content rate of the breast, and calculation of newer thickness information of the breast and newer information of the mammary gland content rate of the breast based on the new absorption coefficient and acquisition of a newer absorption coefficient based on the newer thickness information of the breast and the newer information of the mammary gland content rate of the breast are repeated to calculate the thickness information of the breast and the information of the mammary gland content rate of the breast and acquire the absorption coefficient.

8. The energy subtraction processing method according to claim 7,
wherein the thickness information of the breast is acquired by analyzing at least one of the two radiographic images.

9. The energy subtraction processing method according to claim 7,
wherein the thickness information of the breast is acquired based on a radiographic image acquired with radiation having a low energy distribution between the two radiographic images.

10. The energy subtraction processing method according to claim 7,
wherein, in a case where the breast includes a contrast medium, the thickness information of the breast is calculated by correcting a region of the contrast medium in the two radiographic images.

11. The energy subtraction processing method according to claim 7, further comprising:
correcting the subtraction image using the thickness information of the breast.

12. A non-transitory computer readable recording medium storing an energy subtraction processing program causing a computer to execute:
a step of acquiring two radiographic images with radiations transmitted through a breast and having different energy distributions;
a step of acquiring thickness information of the breast based on at least one of the two radiographic images;
a step of acquiring an absorption coefficient according to the thickness information of the breast;
a step of calculating a weighting coefficient based on the acquired absorption coefficient; and
a step of generating a subtraction image by performing weighting subtraction between corresponding pixels of the two radiographic images using the weighting coefficient,
wherein information of a mammary gland content rate of the breast is further acquired,
the thickness information of the breast and the information of the mammary gland content rate of the breast are calculated based on the two radiographic images and a tube voltage at the time of imaging, an absorption coefficient according to a substance contained in the breast is acquired based on initial values of the thickness information of the breast and the information of the mammary gland content rate of the breast, new thickness information of the breast and new information of the mammary gland content rate of the breast are calculated based on the acquired absorption coefficient, a new absorption coefficient is acquired based on the new thickness information of the breast and the new information of the mammary gland content rate of the breast, and calculation of newer thickness information of the breast and newer information of the mammary gland content rate of the breast based on the new absorption coefficient and acquisition of a newer absorption coefficient based on the newer thickness information of the breast and the newer information of the mammary gland content rate of the breast are repeated to calculate the thickness information of the breast and the information of the mammary gland content rate of the breast and acquire the absorption coefficient.

* * * * *